United States Patent [19]

Janitschke et al.

[11] Patent Number: 4,550,211
[45] Date of Patent: Oct. 29, 1985

[54] PREPARATION OF COMPOUNDS OF THE 4-OXODAMASCONE SERIES, AND NOVEL SCENTS FROM THIS CLASS OF COMPOUNDS

[75] Inventors: Lothar Janitschke, Kleinniedesheim; Werner Hoffmann, Neuhofen, both of Fed. Rep. of Germany

[73] Assignee: BASF Aktiengesellschaft, Ludwigshafen, Fed. Rep. of Germany

[21] Appl. No.: 588,882

[22] Filed: Mar. 12, 1984

[30] Foreign Application Priority Data

Mar. 15, 1983 [DE] Fed. Rep. of Germany ....... 3309169

[51] Int. Cl.$^4$ .................................... C07C 45/42
[52] U.S. Cl. .......................... 568/361; 568/347; 568/378; 568/341; 560/259
[58] Field of Search ............... 568/376, 345, 348, 361, 568/347, 341

[56] References Cited

U.S. PATENT DOCUMENTS

| | | | |
|---|---|---|---|
| 3,927,107 | 12/1975 | Schulte-Elte et al. | 508/376 |
| 3,957,877 | 5/1976 | Schulte-Elte et al. | 508/376 |
| 4,358,614 | 11/1982 | Janitschke et al. | 568/376 |

FOREIGN PATENT DOCUMENTS

| | | | |
|---|---|---|---|
| 3027689 | 2/1982 | Fed. Rep. of Germany | 568/376 |
| 69047 | 6/1975 | Japan | 568/376 |

OTHER PUBLICATIONS

Lowenthol, "Protective Groups in Organic Chem.", pp. 341–343, (1973).
J. March, "Advanced Organic Chemistry", Second Edition, 1977, p. 1082.
Houben-Weyl, "Methoden der Organischen Chemie", 10, (Part 4), p. 268, Stickstoffverbindungen I.
Fieser et al., "Reagents for Organic Synthesis", 1, p. 958.

Primary Examiner—James H. Reamer
Attorney, Agent, or Firm—Oblon, Fisher, Spivak, McClelland & Maier

[57] ABSTRACT

Process for the preparation of the compounds of the formulae Ia and Ib

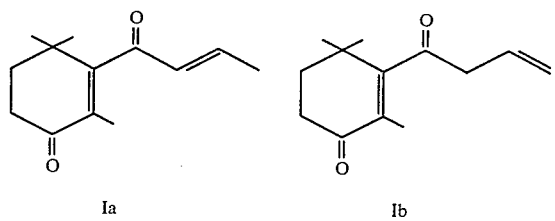

wherein
A. 2,4,4-trimethylcyclohex-2-en-1-one oxime of the formula IIb

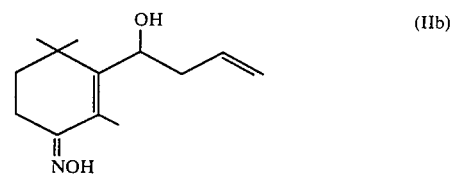

is treated with a strong aqueous acid at from 30° to 80° C., preferably 40° to 70° C.,
B. the resulting ketone of the formula IIIb

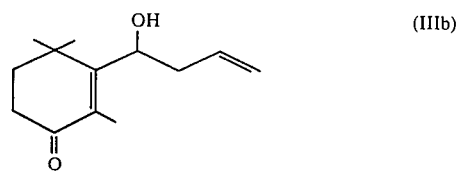

is oxidized in a conventional manner, and
C. if desired, the resulting compound Ib is isomerized in a conventional manner.

Compounds of the formula A

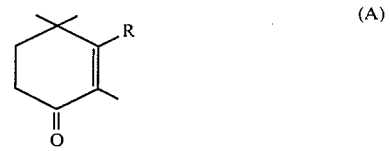

where R is one of the following radicals: —CH(OH)—CH$_2$—CH=CH$_2$ (IIIb), —CH(OH)—CH$_3$ (IIIc), —CH$_2$OH (IIId), —CH(OH)—CH=CH$_2$ (IIIe), —CH(OCOCH$_3$)—CH$_3$ (IIIf), —CH$_2$—OCOCH$_3$ (IIIg), —CO—CH$_2$—CH=CH$_2$ (Ib), —CO—CH$_3$ (Ic) and —CO—CH=CH$_2$ (Ie).

The compounds IIIb to IIIg, Ib, Ic and Ie are useful scents and aromas, and furthermore may become important intermediates for novel carotenoids. They can be prepared in a relatively simple manner from compounds which are very readily available.

7 Claims, No Drawings

PREPARATION OF COMPOUNDS OF THE 4-OXODAMASCONE SERIES, AND NOVEL SCENTS FROM THIS CLASS OF COMPOUNDS

German Laid-Open Application DOS No. 2,353,468 discloses that the compounds of the general formula

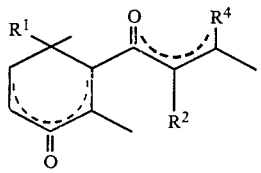

where $R^1$, $R^2$, $R^3$ and $R^4$ are each hydrogen or lower alkyl, and one of the broken lines is a further C—C bond, are useful and important scents. In particular, the stated application describes 2,6,6-trimethyl-1-(1-oxobut-2-en-1-yl)-cyclohex-1-en-3-one (Ia), which is called 4-oxo-damascone, and its two hydrogenation products of the formulae

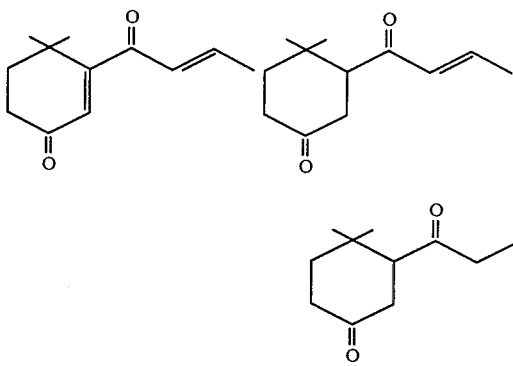

as well as their preparation and their use as scents and flavor materials. The compound Ia is stated to have a characteristic sweet fruity scent which is particularly reminiscent of pears and apples and differs substantially from the somewhat sharp, fruity-minty scent of β-damascone itself. According to the stated German Laid-Open Application, β-damascone is used in each case as a starting material for the preparation of these compounds. Either β-damascone is first converted to an epoxide in the 2,3- or 3,4-position of the ring and this product is then converted to 4-oxodamascone by means of an acid, or damascone is converted with N-bromosuccinimide to damascone brominated in the 3-position of the ring and this product is oxidized with chromium dioxide in glacial acetic acid/water to give Ia.

However, the processes described in the stated application are not yet satisfactory industrially, since the desired compounds have to be prepared starting from a very pure and hence expensive material, ie. damascone, and furthermore are obtained in only moderate yields.

It is an object of the present invention to provide a process by means of which 4-oxodamascone and related compounds can be prepared in good yields from relatively cheap starting materials by a simple and advantageous procedure. It is a further object of the present invention to expand the range of useful scents and aromas by providing interesting novel compounds of the 4-oxodamascone type.

The present invention relates to a process for the preparation of compounds of the formulae Ia and Ib

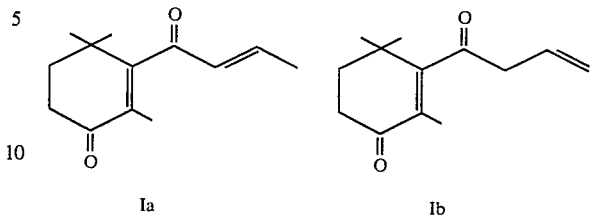

wherein

A. 2,4,4-trimethylcyclohex-2-en-1-one oxime of the formula IIb

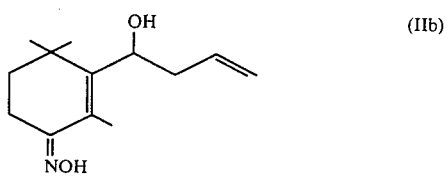

is treated with a strong aqueous acid at from 30° to 80° C., preferably from 40° to 70° C., B. the resulting alcohol of the formula IIIb

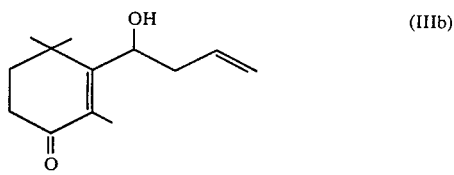

is oxidized in a conventional manner, and

C. if desired, the resulting compound Ib is isomerized in a conventional manner.

The preparation of megastigma-5,7,9-trien-4-one by treating the oxime of the formula IIb with a strong aqueous acid at elevated temperatures has been proposed in Patent Application No. P 32 31 189.3, which has not been previously published. It is surprising that, instead of the megastigmatrienone, the novel ketone IIIb is obtained if the acid treatment is carried out not at the preferred temperature of from 90° to 120° C., in particular from 100° to 115° C., stated in the above patent application, but at from 30° to 80° C., preferably from 40° to 70° C.

The novel ketone of the formula IIIb opens up a very advantageous route to the desirable 4-oxo-β-damascone of the formula Ia, since it is readily available and, on oxidation with, for example, chromosulfuric acid, gives 4-oxo-β-isodamascone of the formula Ib in good yields. This product, which has not yet been characterized physically, can be converted to the desired 4-oxo-β-damascone in a simple manner by acid-catalyzed isomerization.

Starting compounds for the preparation of the compound IIIb, and of the compounds IIIc, IIId and IIIe which are defined below, are the corresponding novel oximes of the general formula II

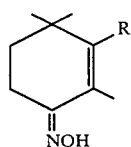

(II)

where R is —CH(OH)—CH$_2$—CH=CH$_2$ (IIb), —CH(OH)—CH$_3$ (IIc), —CH$_2$OH (IId) or —CH(OH)—CH=CH$_2$ (IIe), which in turn can be obtained in excellent yields from 4-oximidocyclocitral of the formula IV

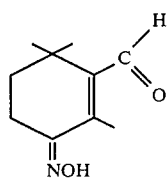

(IV)

by means of a Grignard reaction with the corresponding alkenyl or alkyl Grignard compound or, in the case of IIe, by means of a Meerwein-Ponndorf-Verley reduction with aluminum isopropylate and isobutanol.

The present invention furthermore relates to compounds of the formula A

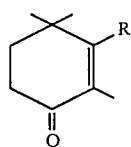

(A)

where R is one of the following radicals: —CH(OH)—CH$_2$—CH=CH$_2$ (IIIb), —CH(OH)—CH$_3$ (IIIc), —CH$_2$OH (IIId), —CH(OH)—CH=CH$_2$ (IIIe), —CH(OCOCH$_3$)—CH$_3$ (IIIf), —CH$_2$—OCOCH$_3$ (IIIg), —CO—CH$_2$—CH=CH$_2$ (Ib), —CO—CH$_3$ (Ic) or —CO—CH=CH$_2$ (Ie).

The compounds IIIb to IIIg, Ib, Ic and Ie are useful scents and aromas, and may furthermore become important intermediates for novel carotenoids. They can be prepared in a relatively simple manner from compounds which are very readily available.

IV can be prepared in a surprisingly simple manner and in high yield from cyclocitral by the process described in the previously unpublished Patent Application No. P 31 37 802.1, and cyclocitral is very advantageously obtainable from citral by the procedure described in German Laid-Open Application DOS No. 3,027,689; this therefore provides a very advantageous overall process for the preparation of 4-oxodamascone and similar good scents and aromas.

When IIb is treated with a strong aqueous acid at about 30°–80° C., preferably about 40°–70° C., the principal product is IIIb, a small amount of megastigma-5,7,9-trien-4-one also being formed. The reaction takes place much more slowly at below 30° C. A particularly suitable strong aqueous acid is 5–50% strength by weight sulfuric acid. 1% strength sulfuric acid can also be used, but with such a dilute acid it is advantageous to choose a somewhat higher temperature. Other suitable strong aqueous acids are solutions or suspensions of phosporic acid, chloroacetic acid and p-toluenesulfonic acid, and suspensions of strongly acidic cation exchangers. The reaction can be carried out either batchwise or continuously.

IIIb, which may be referred to as 4-oxo-β-isodamascol, can be oxidized to 2,4,4-trimethyl-3-(but-3-en-1-on-1-yl)-cyclohex-2-en-1-one (Ib) in a conventional manner, for example with chromosulfuric acid. However, the reaction can also be carried out in a conventional manner using other reagents which are suitable for an oxidation of this type, such as active manganese dioxide, pyridinium chlorochromate, chromium trioxide/pyridine complexes or the like. Regarding detailed information on such oxidations, reference may be made to Jerry March, Advanced Organic Chemistry, 2nd Edition 1977, page 1082, and to the literature cited therein.

Isomerization of the double bond in Ib in a conventional manner, for example under acid catalysis with, for example, p-toluenesulfonic acid, converts Ib to Ia, ie. 2,4,4-trimethyl-3-(but-2-en-1-onyl)-cyclohex-2-en-1-one (Ia; 4-oxo-β-damascone). However, Ib can also undergo isomerization to Ia when the former is distilled, possibly in the presence of traces of an acid (cf. for example Japanese Patent No. 75/69,047 (8.6.1975)).

Using the novel process, it is possible to obtain the desirable 4-oxo-β-damascone Ia without the use of N-bromosuccinimide, in only 3 simple stages, starting from IIb which is obtainable in a simple manner and in high yields. IIb is a more advantageous starting material than the damascone used in the process described in German Laid-Open Application DOS No. 2,353,468.

Other compounds of the 4-oxodamascone series are obtainable in a similar manner.

For example, the novel oximes IIc, IId and IIe can be converted with aqueous ethanolic sodium bisulfite solution to the novel compounds of the formulae IIIc, IIId and IIIe in a conventional manner and in good yield (cf. for example Houben-Weyl, Methoden der organischen Chemie, Vol. 10/IV, page 268 et seq.). The alcohols of the formulae IIIc and IIIc can then be oxidized to the novel compounds 2,4,4-trimethyl-3-acetylcyclohex-2-en-1-one (Ic) and 2,4,4-trimethyl-3-(prop-2-en-1-on-1-yl)cyclohex-2-en-1one (Ie) by a procedure similar to the oxidation of IIIb to Ib, the product being obtained in good yields.

The alcohols IIIc and IIId can be converted to the novel acetates IIIf and IIIe in a conventional manner, for example by reaction with acetic anhydride and pyridine, the products being obtained in very good yields. Regarding further details of such esterification reactions, reference may be made to, for example, Fieser and Fieser, Reagents for Organic Synthesis, Vol. 1, page 958.

The compounds IIIb to IIIg, Ib, Ic and Ie are useful scents and aromas, and furthermore may become important intermediates for novel carotenoids. They can be prepared in a relatively simple manner from compounds which are very readily obtainable.

EXAMPLE 1

A. Preparation of 2,4,4-trimethyl-3-(1-hydroxybut-3-en-1-yl)-cyclohex-2-en-1-one oxime (IIb)

306 g (4 moles) of allyl chloride in 2 liters of absolute tetrahydrofuran were added dropwise to 97.2 g (4 moles) of magnesium and 100 ml of absolute tetrahydrofuran, the Grignard reaction being started by means of a trace of iodine and 1 ml of pure allyl chloride. When the addition was complete, stirring was continued for 1 hour at from 35° to 40° C.

A solution of 181 g (1 mole) of 1-formyl-2,6,6-trimethyl-3-oximidocyclohex-1-ene (IV) in 200 ml of tetrahydrofuran was added dropwise to the resulting solution of allyl magnesium chloride at room temperature. Stirring was then continued for 1 hour at room temperature, after which 400 ml of $H_2O$ were added dropwise at below 10° C., stirring was continued for 15 minutes, the precipitate formed was filtered off under suction and the residue was washed with 3 times 250 ml of $CHCl_3$. The combined filtrates were evaporated down under 20 mbar, and the crystalline residue (207 g, yield of crude product 93%) was recrystallized from 70 ml of cyclohexane.

190 g (yield: 85% of theory) of IIIa of melting point 106°–111° C. were obtained.

B. Preparation of 2,4,4-trimethyl-3-(1-hydroxybut-3-en-1-yl)-cyclohex-2-en-1-one (IIIb)

193 g (0.86 mole) of a 2,4,4-trimethyl-3-(1-hydroxybut-3-en-1-yl)-cyclohex-2-en-1-one oxime (IIb) prepared as described in A were stirred together with 1,900 ml of 30% strength aqueous $H_2SO_4$ for 6 hours at 55° C. The reaction mixture was then cooled to room temperature and extracted several times with methyl t-butyl ether, the combined extracts were dried with sodium sulfate, and the solvent was distilled off under 20 mbar.

164 g (yield: 91.2% of theory) of crude 2,4,4-trimethyl-3-(1-hydroxy-but-3-en-1-yl)-cyclohex-2-en-1-one (IIIb) were obtained. After crude distillation (bp. 62°–142° C./0.5–0.1 mbar), 148 g (yield: 82.3% of theory) of a product were obtained, which was shown by thin-layer chromatography to be slightly impure. Recrystallization from 445 ml of cyclohexane gave 94 g (yield: 52.2%) of a product which was pure according to thin-layer chromatography. Evaporating down the filtrate gave 37.3 g (20.8% of theory) of slightly impure product.

IR (KBr pellet): 3,434 $cm^{-1}$ (OH); 3,078 $cm^{-1}$ (=C—H); 1,656 $cm^{-1}$ (unsaturated C=O); 1,611 $cm^{-1}$, 1,595 $cm^{-1}$ (C=C). $^1H$—NMR ($CDCl_3$/200 MHz) δ: 5.91 ppm, m, 1H, CH—3'; 5.29 ppm, d, 5.28 ppm, d, $CH_2$—4'; 4.55 ppm, d, d (J1~3 Hz, J2, 10 Hz), 1H, CH—1'; 2.49 ppm, t (J 7 Hz), 2H, $CH_2$6; 2.05 ppm, s, broad, 1H, OH; 1.97 ppm, s, 3H, $CH_3$ on C-2; 1.83 ppm, t (J~7 Hz), 2H, $CH_2$—5; 1.33 and 1.23 ppm, 1s in each case, 3H in each case, $CH_3$ on C-4. $^{13}C$—NMR ($CDCl_3$/90.52 MHz) δ: 200.10 ppm, C-1; 163.57 ppm, C-3; 134.94 ppm, C-3'; 131.77 ppm, C-2; 118.14 ppm, C-4'; 70.71 ppm, C-1'; 40.33 ppm, C-2'; 37.86 ppm, C-5; 36.01 ppm, C-4; 34.10 ppm, C-6; 27.28 ppm and 26.14 ppm, $CH_3$ on C-4; 12.54 ppm, $CH_3$ on C-2.

Scent: slightly floral, burnt.

C. Preparation of 2,4,4-trimethyl-3-(but-3-en-1-on-1-yl)-cyclohex-2-en-1-one (Ib)

A solution of 57.8 g (0.19 mole) of $Na_2Cr_2O_7.2H_2O$ in 312 ml of water and 42 ml of concentrated sulfuric acid was added dropwise at 20°–25° C., to a solution of 67 g (0.32 mole) of 2,4,4-trimethyl-3-(1-hydroxybut-2-en-1-yl)-cyclo-hex-3-en-1-one (IIIb), prepared as described in 1B, in 670 ml of diethyl ether. Stirring was continued for 4 hours at from 20° to 25° C., after which the organic phase was separated off, the aqueous phase was extracted with diethyl ether (ether), the combined organic phases were washed with water and with saturated sodium bicarbonate solution and dried with sodium sulfate, and the solvent was distilled off under 20 mbar. 60 g (yield: 90.9% of theory) of 2,4,4-trimethyl-3-(but-3-en-1-on-1-yl)-cyclohex-2-en-1-one were obtained, the product being slightly impure according to thin-layer chromatography. Crystallization from 500 ml of cyclohexane gave 37 g (yield: 56% of theory) of pure product. By distilling off the solvent, a further 21 g (31.8% of theory) of slightly impure product were obtained from the mother liquor.

Mp. 52°–61° C.

Bp.: 116°–120° C./0.5 mbar

IR (KBr pellet):

$^1H$—NMR ($CDCl_3$/100 MHz): 6.21–5.72 ppm, "m", 1H, CH—3'; 5.28–5.02 ppm, "m", 2H, $CH_2$—4'; 3.37 ppm, t, d (J1 2 Hz, J2 7 Hz), 2H, $CH_2$—2'; 2.54 ppm, t (J 7 Hz), 2H, $CH_2$—6, 1.92 ppm, t (J 7 Hz), 2H, $CH_2$—5; 1.65 ppm, s, 3H, $CH_3$ on C-2; 1.23 ppm, s, 6H, $CH_3$ on C-4.

$^{13}C$—NMR ($CDCl_3$/90.52 MHz): 205.47 ppm, C-1'; 198.45 ppm, C-1; 162.44 ppm, C-3; 129.25 ppm, C-3'; 127.95 ppm, C-2; 119.37 ppm, C-4'; 48.95 ppm, C-2'; 38.03 ppm, C-5; 34.44 ppm, C-4; 34.12 ppm, C-6; 27.03 ppm, $CH_3$ on C-4; 12.77 ppm, $CH_3$ on C-13.

Scent: apple.

D. Preparation of 2,4,4-trimethyl-3-(but-2-en-1-on-1-yl)-cyclohex-2-en-1-one (Ia)

153 g (0.74 mole) of 2,4,4-trimethyl-3-(but-3-en-1-on-1-yl)-cyclohex-2-en-1-one (Ib) were stirred under reflux together with 135 ml of ethyl acetate and 3 g of p-toluenesulfonic acid for 2 hours. When the solution had cooled, 1,000 ml of ether were added to it, the mixture was washed with water and with saturated sodium bicarbonate solution and dried with sodium sulfate, and the solvent was distilled off under about 20 mbar. 153 g of 2,4,4-trimethyl-3-(but-2-en-1-on-1-yl)-cyclohex-2-en-1-one (Ia) were obtained, the yield being quantitative, and the product being only slightly impure according to thin-layer chromatography. Recristallization from 500 ml of cyclohexane gave 132 g (yield: 86.8% of theory) of a product which was pure according to thin-layer chromatography; evaporating down the mother liquor gave a further 21 g (yield: 13.2% of theory) of a somewhat impure product.

Scent: sweet, fruity, reminiscent of apples and pears.

EXAMPLE 2

Each of the amounts of 2,4,4-trimethyl-3-(1-hydroxybut-3-en-1-yl)-cyclohex-2-en-1-one oxime (IIb) stated in the Table below were heated, while stirring, with the aqueous acid shown in the Table for the time and at the temperature stated therein. After cooling, the reaction mixture was extracted several times with ether, the combined extracts were washed with saturated $NaHCO_3$ solution and dried with sodium sulfate, and the solvent was distilled off under about 20 mbar. The crude product thus obtained was analyzed by H—NMR spectroscopy or gas chromatography.

TABLE

| Example | IIb [g/mmol] | Aqueous acid [ml or g] | Temperature [°C.] | Time [hours] | Crude product [g] | containing |
|---|---|---|---|---|---|---|
| 2a | 11.05/49.1 | 110 g of 30% strength $H_2SO_4$ | 80 | 6 | 8.9 | about 98% IIIb |
| 2b | 11.15/49.6 | 110 g of 10% strength $H_2SO_4$ | 60 | 3 | 10.7 | about 97% IIIb |

TABLE-continued

| Example | IIb [g/mmol] | Aqueous acid [ml or g] | Temperature [°C.] | Time [hours] | Crude product [g] | containing |
|---|---|---|---|---|---|---|
| 2c | 11.5/51 | 110 g of 30% strength H$_3$PO$_4$ | 60 | 3 | 11 | about 74% IIIb 26% IIb |
| 2d | 11.5/51 | 110 g of 30% strength chloroacetic acid | 60 | 3 | 10 | about 36% IIIb about 64% IIb |
| 2e | 11/48.8 | 110 ml of 30% strength p-toluenesulfonic acid | 60 | 3 | 11 | about 60% IIIb 38% IIb |
| 2f | 11.5/51 | 50 ml of A 15H$^+$ ion exchanger + 50 ml of H$_2$O | 60 | 3 | 6 | about 99.6% IIIb |

EXAMPLE 3

A. Preparation of 2,4,4-trimethyl-3-(1-hydroxyprop-2-en-1-yl)-cyclohex-2-en-1-one oxime (IIe)

A solution of 63.4 g (0.35 mole) of 2,6,6-trimethyl-3-oximidocyclohex-1-en-1-ylcarboxaldehyde (IV) in 300 ml of tetrahydrofuran was added dropwise to a solution of 1.5 moles of vinyl magnesium chloride in 1,000 ml of tetrahydrofuran at from 20° to 25° C. When the addition was complete, stirring was continued for 1 hour at room temperature, after which the reaction mixture was cooled and 150 ml of water were added dropwise at below 10° C. Stirring was then continued for a further 15 minutes.

The precipitated magnesium salts were filtered off, the residue was washed three times with chloroform, and the combined filtrates were evaporated down under about 20 mbar.

83 g of a crude product were obtained, and this was recrystallized from ethyl acetate. 61 g (yield: 83.3% of theory) of spectroscopically pure 2,4,4-trimethyl-3-(1-hydroxyprop-2-en-1-yl)-cyclohex-2-en-1-one oxime were obtained. Evaporating down the mother liquor gave further, impure product (about 20 g). Mp.: 138°-142° C.

B. Preparation of 2,4,4-trimethyl-3-(1-hydroxyprop-2-en-1-yl)-cyclohex-2-en-1-one (IIIe)

36.2 g (0.17 mole) of the 2,4,4-trimethyl-3-(1-hydroxyprop-2-en-1-yl)-cyclohex-2-en-1-one oxime (IIe) obtained as described in A were refluxed with 250 ml of a 40% strength aqueous NaHSO$_3$ solution and 250 ml of ethanol for 2.5 hours.

The ethanol was then distilled off under about 20 mbar, the residue was rendered alkaline with 750 ml of 10% strength NaHCO$_3$ solution and extracted five times with chloroform, the combined extracts were dried with sodium sulfate, and the solvent was distilled off under about 20 mbar.

14.3 g (yield: 42.6% of theory) of IIIe were obtained. The crude product was recrystallized from 43 ml of cyclohexane to give 13.5 g (40.2% of theory) of pure IIIe.

Mp.: 93°-96° C.

IR (KBr pellet): 3,364 cm$^{-1}$, 1,649 cm$^{-1}$, 1,605 cm$^{-1}$ $^1$H—NMR (CDCl$_3$/80 MHz) δ=5.83–6.25 ppm, m, 1H, CH—2'; 5.13–5.42 ppm, m, 2H, CH$_2$—3'; 5.07 ppm, m, 1H, CH—1'; 2.48 ppm, t (J~7 Hz), 2H, CH$_2$—6; 2.12 ppm, m, 1H, OH; 1.87 ppm, s, 3H, CH$_3$ on C-2; 1.81 ppm, t (J~7 Hz), 2H, CH$_2$—5, 1.28 and 1.17 ppm, 1s in each case, 3H, CH$_3$ on C-4.

$^{13}$C—NMR (CDCl$_3$/90.52 MHz) δ: 199.88 ppm, C-1; 161.73 ppm, C-3; 137.98 ppm, C-2'; 132.89 ppm, C-2; 115.91 ppm, C-3'; 71.62 ppm, C-1'; 37.79 ppm, C-5; 36.17 ppm, C-4; 34.20 ppm, C-6; 27.25 and 26.13 ppm, CH$_3$ on C-4; 12.44 ppm, CH$_3$ on C-2.

Scent: sweetish, fruity (woodruff); ionone type without the woody character.

EXAMPLE 4

A. Preparation of 2,4,4-trimethyl-3-(1-hydroxyethyl)-cyclohex-2-en-1-one oxime (IIc)

63.4 g (0.35 mole) of 2,6,6-trimethyl-3-oximidocyclohex-1-en-1-ylcarboxaldehyde (IV) in 300 ml of tetrahydrofuran were reacted with a solution of 1.5 moles of methyl magnesium chloride by a procedure similar to that described in Example 3A.

Working up similarly to Example 3A gave 70 g of a crude product, which was recrystallized from ethyl acetate to give 60 g (yield: 86.9% of theory) of spectroscopically pure 2,4,4-trimethyl-3-(1-hydroxyethyl)-cyclohex-2-en-1-one oxime. Evaporating down the mother liquor gave further product (about 10 g).

Mp.: 131°–135° C.

B. Preparation of 2,4,4-trimethyl-3-(1-hydroxyethyl)-cyclohex-2-en-1-one (IIIc)

39.4 g (0.2 mole) of 2,4,4-trimethyl-3-(1-hydroxyethyl)-cyclohex-2-en-1-one oxime (IIc) were refluxed with 250 ml of a 40% strength NaHSO$_3$ solution and 250 ml of ethanol for 2.5 hours, using a procedure similar to that described in Example 3B.

Working up similarly to Example 3B gave 34.1 g (yield: 93.5% of theory) of crude IIIc, which was recrystallized from 105 ml of cyclohexane to give 24.5 g (yield: 67.2% of theory) of spectroscopically pure, crystalline product.

Mp. 91°–94° C.

IR (KBr pellet): 3,370 cm$^{-1}$, 1,635 cm$^{-1}$, 1,595 cm$^{-1}$.

$^1$H—NMR (CDCl$_3$/80 MHz) δ: 4.72 ppm, d, q (J1~3 Hz, J2~7 Hz), 1H, CH—1'; 2.45 ppm, t (J~7 Hz), 2H, CH$_2$—6; 2.07 ppm, d (J~3 Hz), 1H, OH; 1.95 ppm, s, 3H, CH$_3$ on C-2; 1.83 ppm, t (J~7 Hz), 2H, CH$_2$—5; 1.48 ppm, d (j~7 Hz), 3H, CH$_3$—2'; 1.28 and 1.16 ppm, 1s in each case, 3H, CH$_3$ on C-4.

$^{13}$C—NMR (CDCl$_3$/90.52 MHz) δ: 199.96 ppm, C-1; 164.73 ppm, C-3; 131.54 ppm, C-2; 67.40 ppm, C-1'; 37.90 ppm, C-5; 35.89 ppm, C-4; 34.18 ppm, C-6; 27.43 and 25.95 ppm, CH$_3$ on C-4; 22.26 ppm, C-2'; 12.37 ppm, CH$_3$ on C-2.

Scent: sweetish, fruity (raspberry, woodruff).

EXAMPLE 5

A. Preparation of 2,4,4-trimethyl-3-hydroxymethyl-cyclohex-2-en-1-one oxime (IId)

90.5 g (0.5 mole) of 2,6,6-trimethyl-3-oximidocyclohex-1-en-1-ylcarboxaldehyde (IV) were refluxed with 500 ml of isopropanol and 102 g (0.5 mole) of aluminum triisopropylate. First acetone and then an acetone/isopropanol mixture were distilled off in the course of 1 hour at below 80° C. over a 30 cm column containing V$_2$A stainless steel nets, 60 ml of distillate being obtained. A further 300 ml of isopropanol were then removed by distillation.

The residue was slowly added to a mixture of 1.5 kg of ice and 85 g of concentrated H$_2$SO$_4$. The mixture was extracted five times with chloroform, the extracts were washed neutral with saturated NaHCO$_3$ solution and water and dried with sodium sulfate, and the solvent was distilled off under about 20 mbar. 105 g of crude 2,4,4-trimethyl-3-hydroxymethylcyclohex-2-en-1-one oxime were obtained. The crude product was recrystallized from 500 ml of ethyl acetate to give 91 g (yield: 99.3% of theory) of a pure crystalline compound of melting point 152°–155° C.

Scent: sweetish, fruity (raspberry, woodruff).

B. Preparation of 2,4,4-trimethyl-3-hydroxymethyl-cyclohex-2-en-1-one (IIId)

165 g (0.9 mole) of 2,4,4-trimethyl-3-hydroxymethyl-cyclohex-2-en-1-one oxime (IId) were refluxed with 1,040 ml of 40% strength NaHSO$_3$ solution and 1,040 ml of ethanol for 2.5 hours, using a procedure similar to that described in Example 3B.

Working up similarly to 3B gave 151.1 g (yield: 99.8% of theory) of crude IIId. The product was purified by fractional distillation over a 20 cm column containing V$_2$A stainless steel nets:

Fraction 1: Bp. 88°–103° C./0.02–0.01 mbar, 10 g, 81.2% pure according to gas chromatography Fraction 2: Bp. 103° C./0.01 mbar, 22.1 g, 98.2% pure according to gas chromatography Fraction 3: Bp. 103° C./0.01 mbar, 103.5 g, 100% pure according to gas chromatography.

Fractions 1 to 3 correspond to a total yield of 88.1% of theory, based on 100% pure product.

IR (KBr pellet): 3,376 cm$^{-1}$, 1,647 cm$^{-1}$, 1,615 cm$^{-1}$.

$^1$H—NMR (CDCl$_3$/200 MHz) δ: 3.33 ppm, s, 2H, CH$_2$—OH; 2.50 ppm, t (J~7 Hz), 2H, CH$_2$—6; 1.87 ppm, s, 3H, CH$_3$ on C-2; 1.83 ppm, t (J~7 Hz), 2H, CH$_2$—5; 1.73 ppm, s, 1H, OH; 1.20 ppm, s, 6H, CH$_3$ on C-4.

$^{13}$C—NMR (CDCl$_3$/90.52 MHz) δ: 199.92 ppm, C-1; 160.40 ppm, C-3; 133.08 ppm, C-2; 59.47 ppm, CH$_2$OH; 37.41 ppm, C-5; 35.43 ppm, C-4; 34.33 ppm, C-6; 26.62 ppm, 2CH$_3$ on C-4; 11.31 ppm, CH$_3$ on C-2.

Scent: fruity, floral (somewhat fatty).

EXAMPLE 6

Preparation of 2,4,4-trimethyl-3-(1-acetoxyethyl)-cyclohex-2-en-1-one (IIIf)

114 g (0.63 mole) of 2,4,4-trimethyl-3-(1-hydroxyethyl)-cyclohex-2-en-1-one (IIIc) were refluxed with 59.7 g of pyridine and 64.3 g of acetic anhydride for 3 hours.

The mixture was then cooled, poured onto 1.3 kg of ice water and extracted five times with diethyl ether, the combined extracts were washed several times with water and with saturated NaHCO$_3$ solution and dried with sodium sulfate, and the solvent was distilled off under about 20 mbar.

148.3 g of crude IIIf were obtained and this product was purified by fractional distillation over a bridge.

Fraction 1: Bp. 96° C./0.2–0.15 mbar, 3.6 g, 95.4% pure according to gas chromatography Fraction 2: Bp. 91°–93° C./0.02 mbar, 13.4 g, 96.5% pure according to gas chromatography Fraction 3: Bp. 92°–93° C./0.02 mbar, 93,1 g, 95.8% pure according to gas chromatography Fraction 4: Bp. 93° C./0.02 mbar, 29.3 g, 87.2% pure according to gas chromatography Residue: 1.8 g.

Fractions 1 to 4 together correspond to a yield of 92.8% of theory, based on 100% pure product.

IR (KBr pellet): 1,745 cm$^{-1}$, 1,675 cm$^{-1}$, 1,615 cm$^{-1}$.

$^1$H—NMR (CDCl$_3$/80 MHz) δ: 5.67 ppm, q (J~7 Hz), 1H, CH—1'; 2.47 ppm, t (J~7 Hz), 2H, CH$_2$—6; 2.05 ppm, s, 3H, acetate—CH$_3$; 1.92 ppm, s, 3H, CH$_3$ on C-2; 1.79 ppm, t (J~7 Hz), 2H, CH$_2$—5; 1.51 ppm, d (J 7 Hz), 3H, CH$_3$—2'; 1.29 and 1.18 ppm, 1s in each case, 3H, CH$_3$ on C-4.

$^{13}$C—NMR (CDCl$_3$/90.52 MHz): 199.14 ppm, C-1; 169.54 ppm, carbonyl C of the acetyl group; 160.48 ppm, C-3; 132.41 ppm, C-2; 68.81 ppm, C-1'; 38.05 ppm, C-5; 35.95 ppm, C-4; 34.10 ppm, C-6; 27.76 and 25.90 ppm, CH$_3$ on C-4; 21.01 ppm, acetate CH$_3$; 20.00 ppm, CH$_3$—2'; 12.51 ppm, CH$_3$ on C-2.

Scent: honey, sweet, floral (herbaceous top note).

EXAMPLE 7

Preparation of 2,4,4-trimethyl-3-acetoxymethylcyclohex-2-en-1-one (IIIg)

47 g (0.28 mole) of 2,4,4-trimethyl-3-hydroxymethyl-cyclohex-2-en-1-one (IIId) were refluxed with 26.54 g of pyridine and 28.6 g of acetic anhydride for 3 hours. After cooling, the mixture was poured onto 200 ml of ice water and was extracted five times with ether, the combined extracts were washed several times with saturated NaHCO$_3$ solution and dried with sodium sulfate, and the solvent was distilled off under about 20 mbar.

53.1 g (yield: 90.3% of theory) of crude IIIg were obtained, and this product was purified by fractional distillation over a 20 cm Vigreux column.

Fraction 1: Bp. 58°–84° C./0.03 mbar, 3.4 g, 90.7% pure according to gas chromatography Fraction 2: Bp. 85°–100° C./0.01 mbar, 5.9 g, 93.6% pure according to gas chromatography Fraction 3: Bp. 99° C./0.01 mbar, 36.5 g, 99.9% pure according to gas chromatography Fraction 4: Bp. 99° C./0.01 mbar, 2.2 g, 100.0% pure according to gas chromatography.

Fractions 1 to 4 correspond to a yield of 80.9% of theory, based on 100% pure product.

IR (film): 1,727 cm$^{-1}$, 1,665 cm$^{-1}$, 1,607 cm$^{-1}$.

$^1$H—NMR (CDCl$_3$/80 MHz) δ: 4.65 ppm, s, 2H, CH$_2$—OAc; 2.46 ppm, t (J~7 Hz), 2H, CH$_2$—6; 2.04 ppm, s, 3H, acetyl—CH$_3$; 1.81 ppm, t (J~7 Hz), 2H, CH$_2$—5; 1.78 ppm, s, 3H, CH$_3$ on C-2; 1.17 ppm, s, 6H, CH$_3$ on C-4.

$^{13}$C—NMR (CDCl$_3$/90.52 MHz) δ: 199.61 ppm, C-1; 170.42 ppm, acetyl—C=O; 155.02 ppm, C-3; 135.12 ppm, C-2; 60.98 ppm, CH$_2$ on C-3; 37.44 ppm, C-5; 35.50 ppm, C-4; 34.29 ppm, C-6; 26.54 ppm, CH$_3$ on C-4; 20.70 ppm, acetyl—CH$_3$; 11.44 ppm, CH$_3$ on C-2.

Scent: sweet, fruity, woody.

EXAMPLE 8

Preparation of 2,4,4-trimethyl-3-(prop-2-en-1-on-1-yl)-cyclohex-2-en-1-one (Ie)

A solution of 55 g (0.28 mole) of 2,4,4-trimethyl-3-(1-hydroxyprop-2-en-1-yl)-cyclohex-2-en-1-one (IIIe) in 600 ml of ether was added dropwise, at 20°–25° C., to a mixture of a solution of 250 g of $Na_2Cr_2O_7.2H_2O$ in 1,200 ml of $H_2O$ with 188 ml of concentrated $H_2SO_4$.

When the addition was complete, stirring was continued for 60 minutes at room temperature, after which the organic phase was separated off, the aqueous phase was extracted with chloroform, the combined organic phases were washed several times with water and saturated $NaHCO_3$ solution and dried with sodium sulfate, and the solvent was distilled off under about 20 mbar.

29 g (yield: 53.3% of theory) of crude Ie were obtained. The crude product was recrystallized from 145 ml of cyclohexane to give 23 g (yield: 42.3% of theory) of the pure crystalline compound.

Mp.: 86°–89° C.

IR (KBr pellet): 1,677 $cm^{-1}$, 1,643 $cm^{-1}$, 1,619 $cm^{-1}$, 1,610 $cm^{-1}$.

$^1H$—NMR ($CDCl_3$/100 MHz) δ: 6.00–6.60 ppm, m, 3H, CH—2′, 3′; 2.57 ppm, t (J 7 Hz), 2H, $CH_2$—6; 1.94 ppm, t (J ~ 7 Hz), 2H, $CH_2$—5; 1.61 ppm, s, 3H, $CH_3$ on C-2; 1.21 ppm, s, 6H, $CH_3$ on C-4.

$^{13}C$—NMR ($CDCl_3$/90.52 MHz) δ: 198.49 ppm, C-1; 198.29 ppm, C-1′; 159.90 ppm, C-3; 137.21 ppm, C-3′; 132.36 ppm, C-2′; 129.87 ppm, C-2; 38.03 ppm, C-5; 34.78 ppm, C-4; 34.25 ppm, C-6; 27.25 ppm, $CH_3$ on C-4; 13.13 ppm, $CH_3$ on C-2.

Scent: slightly floral, woody.

EXAMPLE 9

Preparation of 2,4,4-trimethyl-3-acetylcyclohex-2-en-1-one (Ic)

A solution of 70 g (0.38 mole) of 2,4,4-trimethyl-3-(1-hydroxyethyl)-cyclohex-2-en-1-one (IIIc) in 750 ml of ether was added dropwise, at 20°–25° C., to a mixture of a solution of 344 g of $Na_2Cr_2O_7.2H_2O$ in 1,700 ml of $H_2O$ with 260 ml of concentrated $H_2SO_4$.

When the addition was complete, stirring was continued for 1 hour, after which the organic phase was separated off, the aqueous phase was extracted several times with ether, the combined organic phases were washed neutral with saturated NaCl solution and with saturated $NaHCO_3$ solution and dried with sodium sulfate, and the solvent was distilled off under about 20 mbar.

From a total of 4 identical batches, 190 g (yield: 69.3% of theory) of crude Ic were obtained. Distillation over a bridge (bp. 52°–95° C. under 0.35–0.1 mbar) gave 148 g (54.1% of theory) of a product and 30 g of residue, the product being 87.5% pure according to gas chromatography. Pure Ic was obtained by fractional distillation over a 10 cm Vigreux column or by recrystallization from n-hexane.

Mp.: 60°–63° C.

IR (KBr pellet): 1,697 $cm^{-1}$, 1,672 $cm^{-1}$, 1,635 $cm^{-1}$, 1,623 $cm^{-1}$.

$^1H$—NMR ($CDCl_3$/100 MHz) δ: 2.49 ppm, t (J ~ 7 Hz), 2H, $CH_2$—6; 2.21 ppm, s, 3H, acetyl—$CH_3$; 1.87 ppm, t (J ~ 7 Hz), 2H, $CH_2$-5; 1.63 ppm, s, 3H, $CH_3$ on C-2; 1.21 ppm, s, 6H, $CH_3$ on C-4.

$^{13}C$—NMR ($CDCl_3$/90.52 MHz) δ: 205.40 ppm, acetyl—CO; 198.59 ppm, C-1; 162.80 ppm, C-3; 127.36 ppm, C-2; 38.05 ppm, C-5; 34.39 ppm, C-4; 34.12 ppm, C-6; 32.13 ppm, acetyl—$CH_3$; 26.91 ppm, $CH_3$ on C-4; 12.44 ppm, $CH_3$ on C-2.

Scent: woody, slightly floral.

We claim:

1. A process for the preparation of the compounds of the formulae Ia and Ib

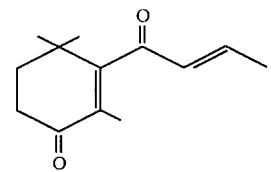 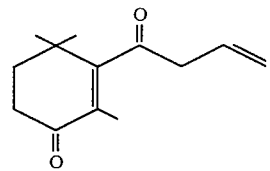

Ia          Ib wherein

A. 2,4,4-trimethylcyclohex-2-en-1-one oxime of the formula IIb

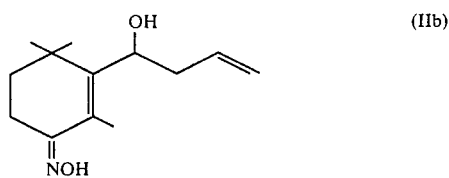

is treated with a strong aqueous acid at from 30° to 80° C.,

B. the resulting ketone of the formula IIIb

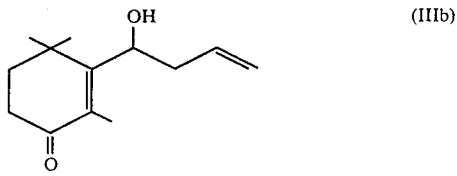

is oxidized in a conventional manner, and

C. if desired, the resulting compound Ib is isomerized in a conventional manner.

2. The process of claim 1, wherein compound IIb is treated with a strong aqueous acid at from 40° to 70° C.

3. The process of claim 1, wherein compound IB is isomerized in a conventional manner.

4. The process of claim 1, wherein the strong aqueous acid is 5 to 50% by weight sulfuric acid.

5. The process of claim 1, wherein the strong aqueous acid comprises (1) a suspension of phosphoric acid, chloroacetic acid and p-toluene sulfonic acid or (2) a suspension of a strongly acidic cation exchanger.

6. The process of claim 1, wherein the reaction is carried out batch-wise.

7. The process of claim 1 wherein the reaction is carried out continuously.

* * * * *